United States Patent
Mirkin et al.

(10) Patent No.: US 11,624,125 B2
(45) Date of Patent: Apr. 11, 2023

(54) STABILIZATION OF COLLOIDAL CRYSTALS ENGINEERED WITH NUCLEIC ACID

(71) Applicant: NORTHWESTERN UNIVERSITY, Evanston, IL (US)

(72) Inventors: Chad A. Mirkin, Wilmette, IL (US); Taegon Oh, Evanston, IL (US); Sarah S. Park, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 81 days.

(21) Appl. No.: 17/272,139

(22) PCT Filed: Sep. 25, 2019

(86) PCT No.: PCT/US2019/052836
§ 371 (c)(1),
(2) Date: Feb. 26, 2021

(87) PCT Pub. No.: WO2020/068905
PCT Pub. Date: Apr. 2, 2020

(65) Prior Publication Data
US 2021/0340692 A1    Nov. 4, 2021

Related U.S. Application Data

(60) Provisional application No. 62/736,260, filed on Sep. 25, 2018.

(51) Int. Cl.
*C30B 7/08* (2006.01)
*C30B 29/02* (2006.01)
*C30B 29/58* (2006.01)

(52) U.S. Cl.
CPC ............... *C30B 29/02* (2013.01); *C30B 7/08* (2013.01); *C30B 29/58* (2013.01)

(58) Field of Classification Search
CPC ............ C30B 29/02; C30B 7/08; C30B 29/58
See application file for complete search history.

(56) References Cited

U.S. PATENT DOCUMENTS 9,376,640 B2 *  6/2016 Cannella ................. C10L 1/06
9,376,690 B2    6/2016 Mirkin et al.
(Continued)

FOREIGN PATENT DOCUMENTS

WO   WO2014201232   * 12/2014
WO   WO2017062646   *  4/2017

OTHER PUBLICATIONS

Chen et al., "Silver-Mediated Double Helix: Structural Parameters for a Robust DNA Building 3lock", Oct. 27, 2017 (Oct. 27, 2017), ACS Omega 2017, 2, 7343-7348, DOI: 10.1021/acsomega. 7b01089; entire document, especially abstract, p. 7347 col. 1 para 1.*

(Continued)

*Primary Examiner* — Robert M Kunemund
(74) *Attorney, Agent, or Firm* — Marshall, Gerstein & Borun LLP

(57) ABSTRACT

A post-synthetic method for stabilizing colloidal crystals programmed from nucleic acid is disclosed herein. In some embodiments, the method relies on $Ag^+$ ions to stabilize the particle-connecting nucleic acid duplexes within the crystal lattice, essentially transforming them from loosely bound structures to ones with very strong interparticle links. In some embodiments, the nucleic acid is DNA. Such crystals do not dissociate as a function of temperature like normal DNA or DNA-interconnected colloidal crystals, and they can be moved from water to organic media or the solid state, and stay intact. The $Ag^+$-stabilization of the nucleic acid (e.g., DNA) bonds is accompanied by a nondestructive contraction of the lattice, and both the stabilization and (Continued)

contraction are reversible with the chemical extraction of the $Ag^+$ ions, e.g., by AgCl precipitation with NaCl.

18 Claims, 10 Drawing Sheets

Specification includes a Sequence Listing.

(56) References Cited

U.S. PATENT DOCUMENTS

| | | | | |
|---|---|---|---|---|
| 2002/0018611 A1* | 2/2002 | Maleki | ............... | G02B 6/34 |
| | | | | 372/92 |
| 2013/0261292 A1* | 10/2013 | Gang | ............... | C07H 21/04 |
| | | | | 536/23.1 |
| 2016/0177381 A1* | 6/2016 | Gu | ............... | C12Q 1/6827 |
| | | | | 506/9 |
| 2016/0031897 A1 | 11/2016 | Pine et al. | | |
| 2017/0321280 A1* | 11/2017 | Vo-Dinh | ............... | C12Q 1/6886 |

OTHER PUBLICATIONS

International Search Report and Written Opinion for Corresponding International Application No. PCT/US2019/052836 dated Dec. 16, 2019.
Nykypanchuk et., "DNA-guided Crystallization of colloidal nanoparticles" Nature, vol. 451, pp. 549-552, Jan. 31, 2008.
Chen et al., "Silver-Medicated Double Helix: Structural Parameters for a Robust DNA Building Block", ACS Omega 2017, 2, pp. 7343-4348, Oct. 27, 2017.
Mirkin et al., "A DNA-based method for rationally assembling nanoparticles into macroscopic materials" Nature, vol. 382, pp. 607-609, Aug. 15, 1996.
Park et al., "DNA-programmable nanoparticles crystallization" Nature, vol. 451, pp. 553-556, Jan. 31, 2008.
Macfarlane et al., Nanoparticles Superlattice Engineering with DNA Science, vol. 334, pp. 204-208, Oct. 14, 2011.
Auyeung et al., "DNA-mediated nanoparticle crystallization into wulff polyhedra" Nature, vol. 505, pp. 73-77, Jan. 2, 2014.
O'Brien et al., "Programming Colloidal Crystal Habit with Anisotropic Nanoparticle Building Blocks and DNA Bonds" Journal American Chemical Society, vol. 138, pp. 14562-14565, Oct. 28, 2016.
Cigler et al., "DNA-controlled assembly of a NaTl lattice structure from gold nanoparticles and protein nanoparticles" Nature Materials, vol. 9, pp. 918-822, Nov. 2010.
Zhang et al., "A general strategy for the DNA-mediated self-assembly of functional nanoparticles into heterogeneous systems" Nature Nanotechnology, vol. 8, Nov. 2013.
Wang et al., "Synthetic Strategies Toward DNA-Coated Colloids that Crystallize" Journal American Chemical Society, vol. 137, pp. 10760-10766, Jul. 20, 2015.
Auyeung et al., "Transitioning DNA-Engineered Nanoparticles Superlattices from Solution to the Sold State" Advance Materials, vol. 24, pp. 5181-5186, 2012.
Swasey et al., "Silver (I) as DNA glue: Ag+-mediated guanine pairing revealed by removing Watson-Crick constraints" Scientific Reports, vol. 5, pp. 1-9, May 14, 2015.
Liu et al., "A DNA Structure Containing $Ag^I$ -Mediated G:G and C:C Base Pairs" Angewandte Chem. International Edition, vol. 56, pp. 9430-9434, 2017.
Swasey et al., "Silver-mediated base pairings: towards dynamic DNA nanostructures with enhanced chemical and thermal stability" New Journal of Physics, vol. 18, pp. 1-14, 2016.
Ennifar et al., "A crystallographic study of the binding of 13 metal ions to two related RNA duplexes" Nucleic Acids Research, vol. 31, No. 1, pp. 2671-2682, Mar. 13, 2003.
Miyake et al., "$Mercury^{II}$-Mediated Formation of Thymine-$Hg^{II}$-Thymine Base Pairs in DNA Duplexes" J. Am. Chem. Soc, pp. 2172-2173, vol. 128, No. 7, 2006.
Ono et al., "Specific interactions between silver(I) ions and cytosine-cytosine pairs in DNA Duplexes" Chemical Communication, pp. 4825-4827, Aug. 22, 2008.
Urata et al., "Pyrimidine-pyrimidine base pairs stabilized by silver(I) ions" Chemical Communication, vol. 47, pp. 941-943, Nov. 15, 2010.
Funai et al., "$Ag^I$ Ion Mediated Formation of a C-A Mispair by DNA Polymerase" Angewandte Chemical International Edition, vol. 51, pp. 6464-6466, 2012.
Kondo et al., "A metallo-DNA nanowire with uninterrupted one-dimensional silver array" Nature Chemistry, vol. 9, pp. 956-960, Oct. 2017.
Jones et al.," Programmable materials and the nature of the DNA bond" Science, vol. 347, Issue 6224, 1260901 (2015).
Oh et al., "Density-Gradient Control over Nanoparticle Supercrystal Formation" Nano Lett. 2018, vol. 18, 6022-6029.
Mason et al., "Contraction and Expansion of Stimuli-Responsive DNA Bonds in Flexible Colloidal Crystals" J. Am. Chem. Soc. 2016, 138, 8722-8725.
Williamson et al., "X-Ray Line Broadening From Filled Aluminum and Wolfram" Acta Metallurgica, vol. 1, pp. 22-33, Jan. 1953.
Volkov et al., DNA with Ionic, Atomic, and Clustered Silver: An XPS Study The Journal of Physical Chemistry, 2017, vol. 121, pp. 2400-2406.
Izatt et al., Sites and Thermodynamic Quantities Associated with Proton and Metal Ion Interaction with Ribonucleic Acid, Deoxyribonucleic Acid, and Their Constituent Bases, Nucleosides, and Nucleotides Chemical Reviews, 1971, vol. 71, No. 5.
Okamoto et al., "Metal-Ion Selectivity of Chemically Modified Uracil Pairs in DNA Duplexes" Angew. Chem. Int, Ed, 2009, vol. 48, pp. 1648-1651.
Park et al., "Plasmonic photonic crystals realized through DNA-programmable assembly" PNAS, Jan. 27, 2015, vol. 112, No. 4, pp. 977-981.
Ross et al., "Optical Properties of One-, Two-, and Three-Dimensional Arrays of Plasmonic Nanostructures" The Journal of Physical chemistry, 2016, vol. 120, pp. 816-830.
Sun et al., Design principles for photonic crystals based on plasmonic nanoparticle superlattices PNAS, Jul. 10, 2018, vol. 115, No. 28, pp. 7242-7247.
Auyeung et al., "Controlling Structure and Porosity in Catalytic Nanoparticle Superlattices with DNA" J. Am. Chem. Soc. 2015, vol. 137, pp. 1658-1662.
Choi et al., "Exploiting the colloidal nanocrystal library to construct electronic devices" Science, vol. 352, Issue 6282, pp. 205-208, Apr. 8, 2016.
Auyeung et al., Synthetically programmable nanoparticle superlattices using a hollow three-dimensional space approach Nature Nanotechnology, vol. 7, Jan. 2012, pp. 24-28.
Hurst et al., Maximizing DNA Loading on a Range of Gold Nanoparticles Sizes Analytical Chemistry, vol. 178, No. 24, Dec. 15, 2006, pp. 8313-8318.

* cited by examiner

SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: A Anchor
<220> FEATURE:
<221> NAME/KEY: misc_feature
<222> LOCATION: (18)..(18)
<223> OTHER INFORMATION: (Spacer 18)2- (CH2)3SH

<400> SEQUENCE: 1
tcaactattc ctacctac                                                 18

<210> SEQ ID NO 2
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: A Linker
<220> FEATURE:
<221> NAME/KEY: misc_feature
<222> LOCATION: (18)..(18)
<223> OTHER INFORMATION: Spacer 18

<400> SEQUENCE: 2
gtaggtagga atagttgatt tcctt                                         25

<210> SEQ ID NO 3
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: B Anchor
<220> FEATURE:
<221> NAME/KEY: misc_feature
<222> LOCATION: (18)..(18)
<223> OTHER INFORMATION: (Spacer 18)2 - (CH2)3SH

<400> SEQUENCE: 3
tccactcata ctcagcaa                                                 18

<210> SEQ ID NO 4
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: B Linker
<220> FEATURE:
<221> NAME/KEY: misc_feature
<222> LOCATION: (18)..(18)
<223> OTHER INFORMATION: (Spacer 18)

<400> SEQUENCE: 4
ttgctgagta tgagtggaaa ggaaa                                         25

```
<210> SEQ ID NO 5
<211> LENGTH: 45
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Long A Linker
<220> FEATURE:
<221> NAME/KEY: misc_feature
<222> LOCATION: (18)..(18)
<223> OTHER INFORMATION: (Spacer 18)
<220> FEATURE:
<221> NAME/KEY: misc_feature
<222> LOCATION: (18)..(18)
<223> OTHER INFORMATION: (Spacer 18)

<400> SEQUENCE: 5
gtaggtagga atagttgatt actgagcagc actgattttt tcctt            45

<210> SEQ ID NO 6
<211> LENGTH: 45
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Long B Linker
<220> FEATURE:
<221> NAME/KEY: misc_feature
<222> LOCATION: (18)..(18)
<223> OTHER INFORMATION: (Spacer 18)
<220> FEATURE:
<221> NAME/KEY: misc_feature
<222> LOCATION: (38)..(38)
<223> OTHER INFORMATION: (Spacer 18)

<400> SEQUENCE: 6
ttgctgagta tgagtggatt actgagcagc actgatttaa ggaaa            45

<210> SEQ ID NO 7
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Self-Complementary A Linker
<220> FEATURE:
<221> NAME/KEY: misc_feature
<222> LOCATION: (18)..(18)
<223> OTHER INFORMATION: (Spacer 18)

<400> SEQUENCE: 7
gtaggtagga atagttgagc gc                                     22

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Duplexer for Block modular unit

<400> SEQUENCE: 8
aaatcagtgc tgctcagtaa                                        20
```

US 11,624,125 B2

STABILIZATION OF COLLOIDAL CRYSTALS ENGINEERED WITH NUCLEIC ACID

CROSS-REFERENCE TO RELATED APPLICATIONS

This application is a U.S. National Stage of International Patent Application No. PCT/US2019/052836 filed Sep. 25, 2019, which in turn claims the benefit of U.S. Provisional Patent Application No. 62/736,260 filed on Sep. 25, 2018, the disclosure of which are each hereby incorporated by reference in their entireties.

STATEMENT OF GOVERNMENT SUPPORT

This invention was made with government support under FA9550-17-1-0348 awarded by the Air Force Office of Scientific Research; FA2386-13-1-4124 awarded by the Asian Office of Aerospace Research and Development; and DE-SC0000989 awarded by the Department of Energy. The government has certain rights in the invention.

INCORPORATION BY REFERENCE OF MATERIALS SUBMITTED ELECTRONICALLY

This application contains, as a separate part of the disclosure, a Sequence Listing in computer readable form (Filename: 2018-152_Seqlisting.txt; Size: 2,967 bytes; Created: Feb. 25, 2021), which is incorporated by reference in its entirety.

BACKGROUND

DNA-mediated colloidal crystal engineering is emerging as one of the most powerful ways to deliberately generate and tailor crystal composition, lattice parameter, and habit.[1] However, such structures are held together by relatively weak linkages that are sensitive to the environment (salt concentration, solvent, and temperature). As a consequence, they typically must be embedded in a matrix, such as silica, before they can be manipulated and studied in the solid state.[2] A need exists for methods of making colloidal crystals that exhibit improved stability and can be used in a myriad of applications.

SUMMARY

Provided herein are methods comprising admixing a colloidal crystal with a silver ion source to form a stabilized colloidal crystal, wherein the colloidal crystal comprises nanoparticles modified on the nanoparticle surface with nucleic acids ("anchor strands") and arranged in a lattice pattern; and the stabilized colloidal crystal exhibits a lattice parameter (Å) of at least 15% smaller than that of the colloidal crystal, and exhibits improved stability in one or more of the following: water, an organic solvent, a pH of 5 to 11, a temperature of 25° C. to 200° C.; or in a solid state compared to the colloidal crystal.

DETAILED DESCRIPTION

Figure 1:
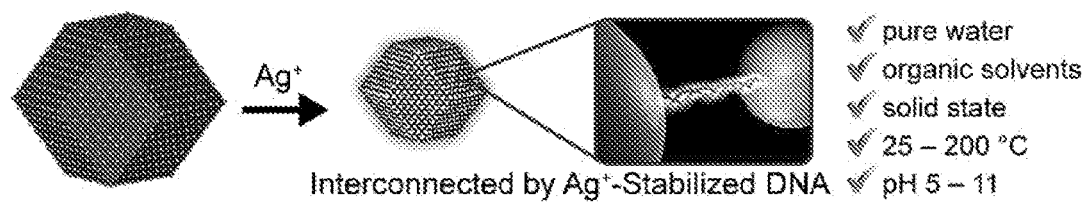
FIG. 1 is a schematic depiction of post-synthetic method for stabilizing nucleic acid (e.g., DNA)-interconnected colloidal crystals with $Ag^+$.

Provided herein are methods comprising admixing a colloidal crystal with a silver ion source to form a stabilized colloidal crystal, wherein the colloidal crystal comprises nucleic acid surface-functionalized nanoparticles arranged in a lattice pattern; and the stabilized colloidal crystal exhibits a lattice parameter (Å) of at least 15% smaller than that of the colloidal crystal, and exhibits improved stability in one or more of the following: water, an organic solvent, a pH of 5 to 11, a temperature of 25° C. to 200° C.; or in a solid state compared to the colloidal crystal.

As used herein, the term "colloidal crystal" refers to a material formed from nanoparticles having nucleic acids appended to their surface (an anchor strand), wherein the nucleic acids, optionally in the presence of a linker strand, assemble to form a lattice pattern. The colloidal crystals are also referred to as PAEs herein. The assembly of the nanoparticles to different lattice patterns can be achieved based upon selection of the sequences of anchor strands on the surfaces of the nanoparticles and optional linker strand. In some cases, the linker strand comprises a nucleic acid and a polyethylene glycol spacer. In some cases, the anchor strand further comprises a polyethylene glycol spacer. An ethylene glycol spacer can comprise three to twenty-five ethylene glycol units, e.g., 2 to 15, 3 to 10, 5 to 15, 5 to 10, 2 to 10, 10 to 15, 2, 3, 4, 5, 6, 7, 8, 9, 10, 11, 12, 13, 14, or 15 ethylene glycol units. The nucleic acids used herein can, in some embodiments, comprise DNA, or RNA, and can comprise natural and/or unnatural nucleobases. The anchor strands are modified at one terminus so that they can associate with the nanoparticle surface (e.g., a thiol moiety to bond to a gold nanoparticle surface).

The silver ion source can be any suitable silver salt. In some cases, the silver ion source is silver nitrate.

The colloidal crystal and the silver ion source can be admixed at, e.g., room temperature (25° C.) to 100° C. In some cases, they are mixed at room temperature for 12 to 36 hours. In some cases, they are mixed at 85° C. to 100° C. (e.g., 85° C. to 95° C., 85° C. to 90° C. or 90° C. to 95° C.) for one to 90 minutes, or for 5 to 60 minutes, 10 to 45 minutes, 5 to 30 minutes, or 10 to 30 minutes.

The stabilized colloidal crystals can be washed after formation, e.g., with water.

In some cases, the colloidal crystal is prepared by admixing a solution of a first nanoparticle and a second nanoparticle, optionally in the presence of a linker strand, under conditions to form the colloidal crystal via hybridization of the first nanoparticle and the second nanoparticle, and optionally the linker strand, wherein the first nanoparticle anchor strand, the second nanoparticle anchor strand, and optionally the linker strand comprise complementary sequences to hybridize. In some cases, the solution is cooled from a temperature of (i) 50° C. to 75° C. down to (ii) room temperature. The rate of cooling can be, e.g., 0.01° C./min to 0.1° C./min.

In embodiments where a linker strand is used, the linker strand can comprises a nucleic acid sequence sufficiently complementary at a first portion of the linker strand to hybridize with the first nanoparticle anchor strand and sufficiently complementary at a second portion of the linker strand to hybridize with the second nanoparticle anchor strand. In some cases, the linker strand comprises a polyethylene glycol spacer as discussed above. In some cases, the solution of first nanoparticle and second nanoparticle and optional linker strand is admixed above a dextran sulfate aqueous solution such that the colloidal crystals precipitate into the dextran sulfate aqueous solution. In some cases, the dextran sulfate aqueous solution is a 10% dextran sulfate aqueous solution. In some cases, the colloidal crystals are isolated from the solution, e.g., via filtration. In some cases, the colloidal crystals are dried.

The stabilized colloidal crystal prepared by the disclosed methods has a smaller lattice parameter than the corresponding starting colloidal crystal. Without being bound by theory, it is hypothesized that the silver ion creates a stronger and/or shorter ionic bond between the nucleic acid strands of the colloidal crystal than the corresponding hydrogen bonds. The lattice parameter is smaller by at least 15%, at least 20%, at least 25%, up to 25%, or 15 to 15% in the stabilized colloidal crystal compared to the colloidal crystal. The stabilized colloidal crystal can be more stable than the colloidal crystal. For example, when exposed to water, the colloidal crystal can decompose to its starting nanoparticle components while the stabilized colloidal crystal maintains its lattice structure. Stability can be assessed in the presence of different solvents (e.g., acetone, ethanol, isopropyl alcohol, water). Stability can also be assessed at different temperatures and pHs or buffers. The stabilized colloidal crystal can be more stable at pHs of 5, 6, 7, 8, 9, 10, and/or 11, compared to that of the colloidal crystal. The stabilized colloidal crystal can be more stable at a wide range of temperatures, e.g., 25° C. to 200° C., 25 to 100° C., 50° C. to 200° C., 50° C. to 100° C., and/or 100° C. to 200° C., compared to that of the colloidal crystal. The stabilized colloidal crystal can be more stable in the presence of different salts and/or buffers compared to that of the colloidal crystal. Stability can be determined via an analytical assessment—such as XPS, SAXS, SEM, CD, color change, UV-vis spectrometry, as detailed in the examples section below.

Discussion: Herein, a post-synthetic approach to increase the stability of nucleic acid (e.g., DNA)-interconnected colloidal crystals is provided. In any of the aspects or embodiments of the disclosure, the nucleic acid is DNA. From recent studies, it has been shown that the thermal stability of duplexed oligonucleotides can be increased by the insertion of Ag+ ions in between the nucleobases.[3] Specifically, Ag$^+$ ions replace the hydrogen bonds between the base pairs and form coordinate covalent bonds between Ag$^+$ ions and heterocyclic N atoms of the nucleobases. In contrast with other metal ions which form one specific metallo base pair (e.g., G-Au$^{3+}$—C and T-Hg$^{2+}$-T),[4] Ag$^+$ is less specific and results in a variety of metallo base pairs such as C—Ag$^+$—C, C—Ag$^+$-T, C—Ag$^+$-A, G-Ag$^+$-G, G-Ag$^+$—C, and T-Ag$^+$-T and is, therefore, has the ability to fully metallize DNA duplex strands.[3c, 5] The present disclosure provides methods for Ag$^+$-stabilization of nucleic acid (e.g., DNA) and its use in stabilizing colloidal crystals made from DNA and DNA-modified nanoparticles, often referred to as programmable atom equivalents (PAEs).[6] The compositions and methods of the disclosure eliminate the need for a stabilizing matrix to work with such systems in non-aqueous environments or the solid state (see FIG. 1).

Nanoparticle colloidal crystals synthesized by DNA-based colloidal crystal engineering are only stable in aqueous salt solution and sensitive to salt, temperature, solvent. The techniques disclosed herein result in structures that provide several major advantages over previous matrix-based encapsulation methods. First, it does not perturb the crystal symmetry or habit. Second, it results in structures that can be transferred to media normally incompatible with DNA (e.g., organic solvents, pure water, and the solid state). Third, it allows one to more cleanly image the 3D crystals by electron microscopy methods, providing greater information about these fascinating architectures. Finally, methods that increase both the quality and robustness of colloidal crystals engineered with nucleic acid (e.g., DNA) are essential for producing architectures that become the components of many devices.

Thus, as explained above, the disclosure provides a post-synthetic method for stabilizing nucleic acid-interconnected colloidal crystals with $Ag^+$. In any of the aspects or embodiments of the disclosure, the nucleic acid is DNA. Thus, in any of the aspects or embodiments provided herein, the disclosure provides a post-synthetic method for stabilizing DNA-interconnected colloidal crystals with $Ag^+$. The $Ag^+$ increases the strength of the DNA bonds, and the resulting colloidal crystals can be transferred into pure water, organic solvents, and the solid state. They are highly resistant to structural changes over the room temperature to 200° C. range, and pH over the 5-11 range. The compositions and methods of the disclosure allow for the study of crystals in environments that are incompatible with structures made by conventional DNA programmable methods and without the influence of a matrix like silica.

Figure 2:
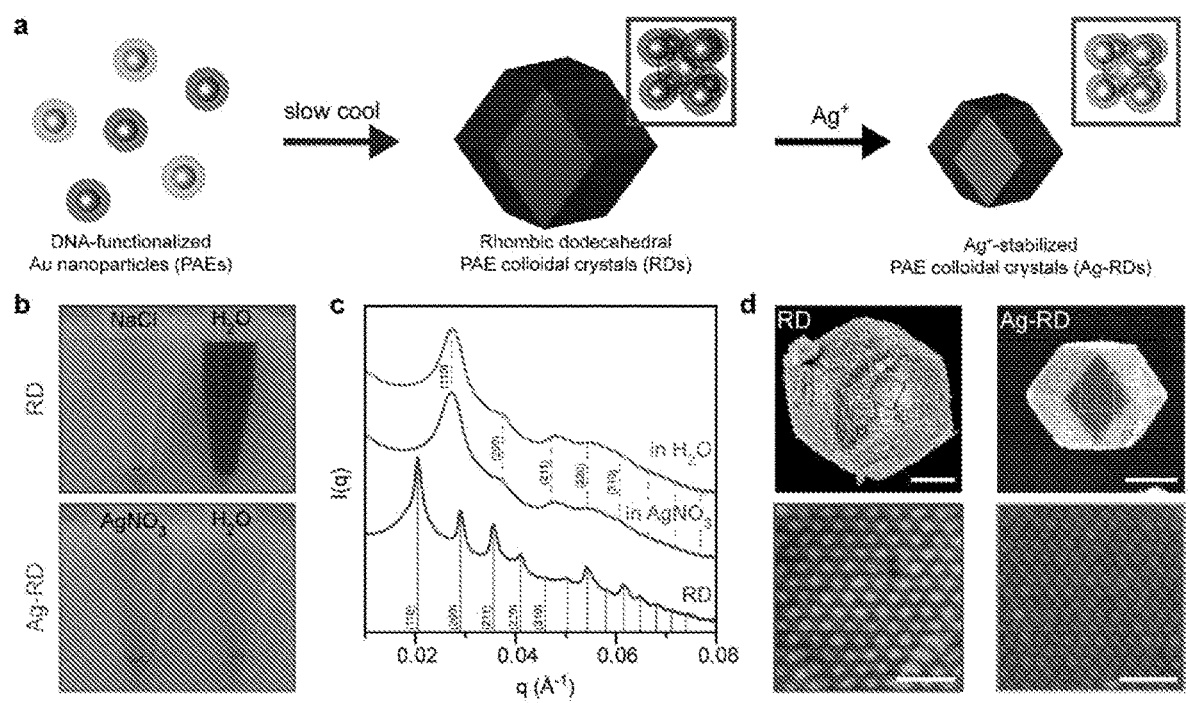
FIG. 2 shows (a) Schematic illustrating the synthesis of $Ag^+$-stabilized PAE crystals (Ag-RDs). (b) In contrast to unmodified PAE crystals (RDs), which are stable in 0.5 M NaCl but dissociate upon resuspension in pure water, Ag-RDs are stable in water. (c) Radially-averaged one-dimensional SAXS patterns show lattice contraction upon the transformation into Ag-RDs (green) by transferring RDs (purple) to 0.5 M $AgNO_3$. Ag-RDs are stable in unsalted water (grey). The first five peaks in each pattern were assigned to bcc lattices. (d) SEM micrographs (bottom: high resolution images of (110) facets from the corresponding squares) confirm the nondestructive contraction of RD to Ag-RD while maintaining crystallinity. Scale bars: (top) 500 nm and (bottom) 100 nm.
Figure 6:
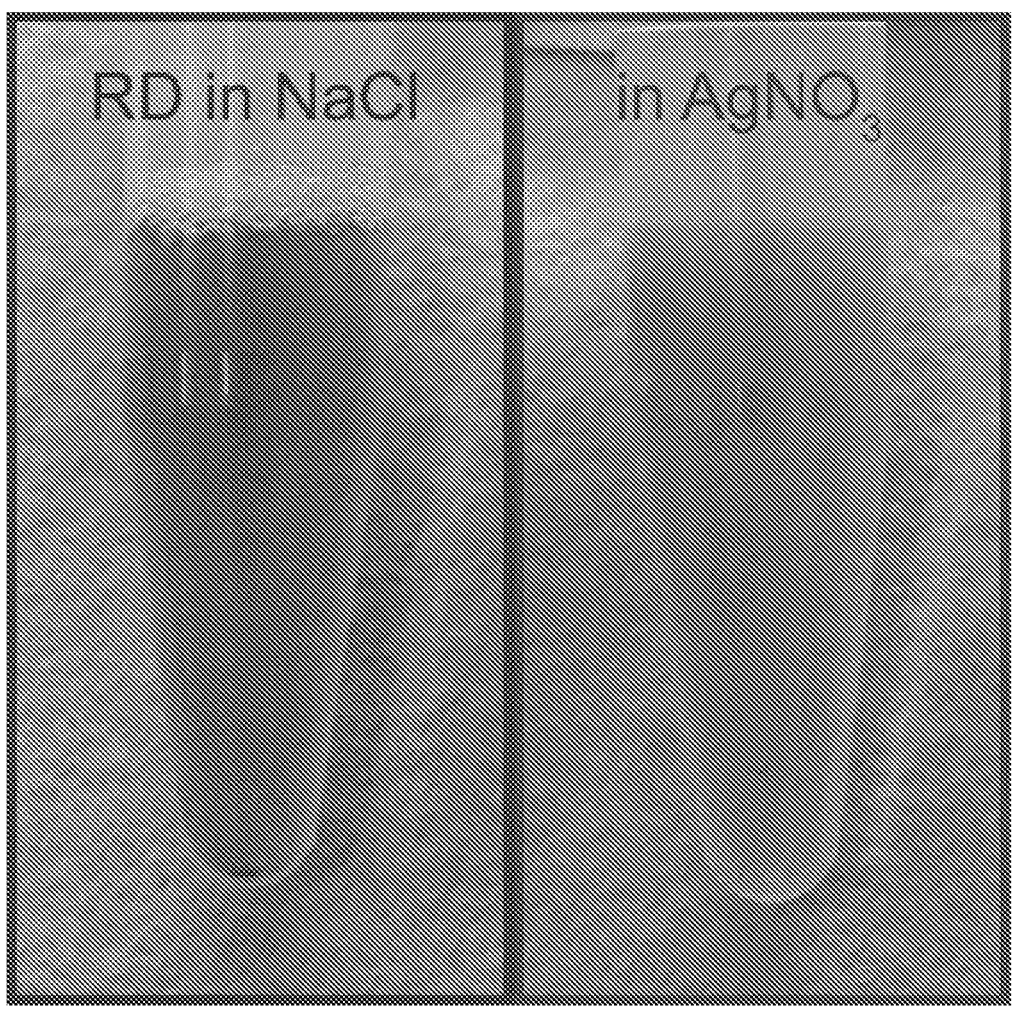
FIG. 6 shows a photograph of two tubes containing the same amount of RDs suspended in 0.5 M NaCl (left) and in 0.5 M AgNO3 (right), where reduced light scattering is observed with the $Ag^+$-treatment.

Colloidal single crystals of nanoparticles (e.g., PAEs) can be synthesized using methods described in the literature for making body centered cubic (bcc) structures.[1d, 7] Specifically, complementary A and B type PAEs (spherical Au nanoparticles with 20 nm diameters, DNA sequences in Table 1) were mixed together and slowly cooled in pH-buffered saline (0.5 M NaCl). Through this process, the PAEs crystallize into superlattices and eventually form rhombic dodecahedral (RD) colloidal crystals. After $Cl^-$ anions were removed by repeated solution exchange with 0.5 M $NaClO_4$ (aq) to avoid any precipitation with $Ag^+$, the RDs were dispersed in 0.5 M $AgNO_3$ solution, where excess $Ag^+$ ions compared to the DNA base pairs were present. At this stage, the effect of $Ag^+$-stabilization can be observed with the naked eye, since the dark suspension of RDs immediately becomes less opaque upon redispersion (FIG. 6). This change is caused by the contraction of the DNA particle interconnects, resulting in a reduction of the visible light scattering cross-section of the crystals. Small-angle X-ray scattering (SAXS) confirms this contraction with peak-shifts to higher q, a consequence of the decrease in lattice parameter (a 25% reduction, Table 3). This contraction occurs due to a shortening of the metallo-DNA duplex, compared to the metal-free form, which has been crystallographically characterized.[3c] The peak broadening in SAXS that accompanies the $Ag^+$ addition can be attributed to an increase in lattice strain and reduction in domain size, both of which result from the volume contraction of the colloidal crystals (FIG. 2c).[8] Scanning electron microscopy (SEM) also showed that the RDs retained their rhombic dodecahedron crystal habit and bcc lattice symmetry (FIG. 2d). Importantly and remarkably, the $Ag^+$-stabilized PAE crystals (Ag-RDs) can be transferred to pure water without them disassembling, something not possible with untreated DNA-interconnected RDs, which disassemble into colloidal suspensions of particles, as evidenced by the formation of a red colloid with a UV-vis signature at 520 nm associated with dispersed 20 nm diameter Au nanoparticles (FIG. 2b).

Figure 7:
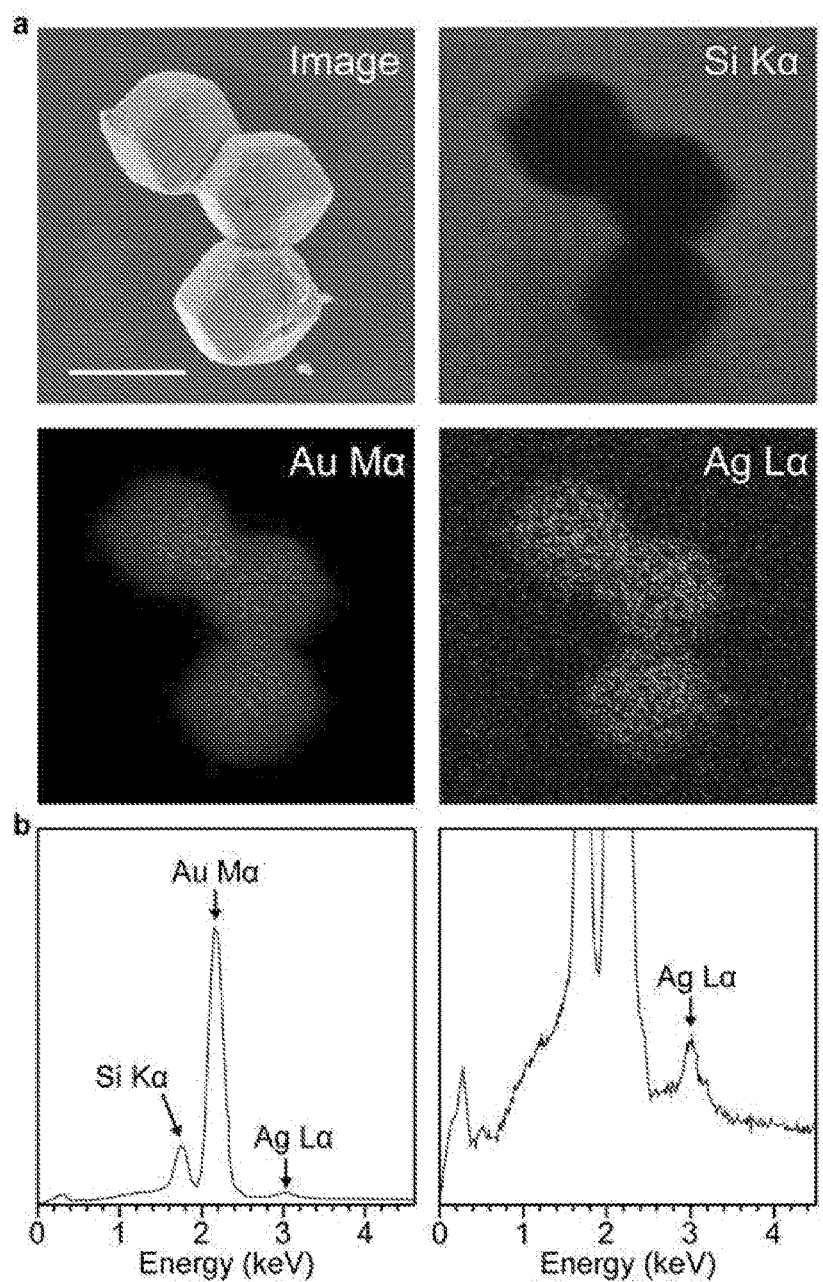
FIG. 7 shows (a) SEM and SEM-EDX images of Ag-RDs with elemental mapping of Si, Au, and Ag. Scale bar: 1 µm. (b) EDX spectrum with the beam focused on the cross noted in panel a, with a magnified plot for Ag signal.

The structural stability of Ag-RDs in pure water was further verified by SAXS, which showed no peak shift (FIG. 2c). Also, after three cycles of washing with pure water and drying, the lattice symmetry and microscale crystal habit of the Ag-RDs were not significantly affected by the $Ag^+$ ion-induced transition to the solid state, as evidenced by SEM (note that unlike silica matrix embedding, there was no evidence of impurity-based precipitates, FIGS. 2d and 7). Note that an additional 15% reversible decrease in lattice parameters is observed by SAXS with this dehydration process (therefore in total, a 36% contraction from the as-synthesized RDs, FIG. 8a and Table 3). The dehydration-induced shrinkage was attributed to the polyethylene glycol (PEG) units in the DNA; only a 3.2% contraction, upon dehydration, was observed in the $Ag^+$-ion stabilized PAE crystals without the PEG units in the anchor strands (FIG. 9b and Table 3). The mean edge lengths of the rhombic dodecahedra PAE crystals, post-stabilization, were measured by solid-state SEM; for silica-embedded samples, the average was determined to be 0.93±0.16 μm, while for Ag-RDs, it was determined to be 0.61±0.09 μm.[2] These microscopic contraction values correspond well with the lattice parameter changes determined by SAXS (i.e., a 34% decrease for the rhombic dodecahedron edge lengths in SEM and a 36% decrease in the lattice parameters as measured by SAXS, Table 3).

Figure 10:
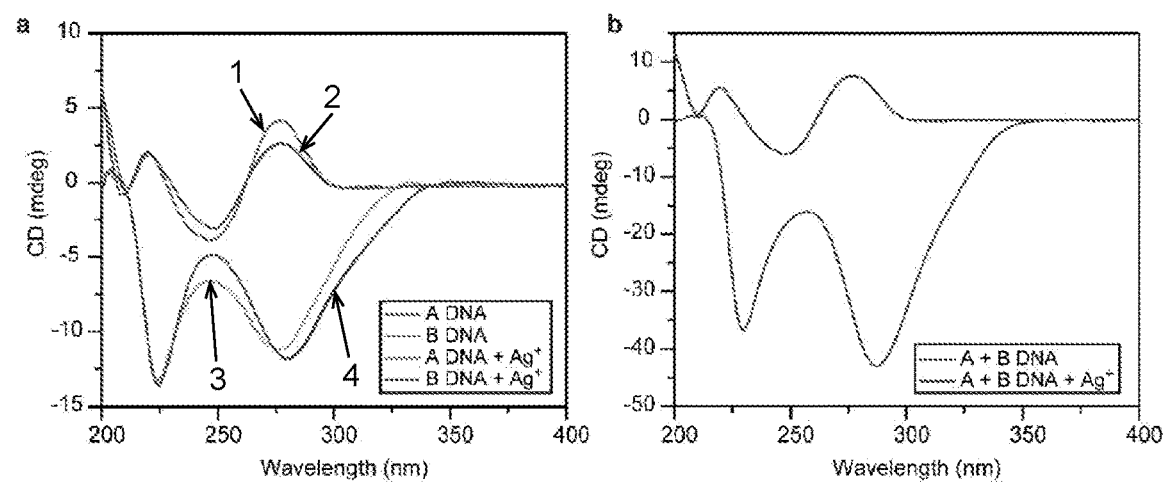
FIG. 10 shows CD spectra of (a) A DNA (anchor+linker) (trace 1), B DNA (trace 2), A DNA with $Ag^+$ (trace 3), and B DNA with $Ag^+$ (trace 4), and (b) mixture A DNA and B DNA with (top trace) and without $Ag^+$ (bottom trace).
Figure 11:
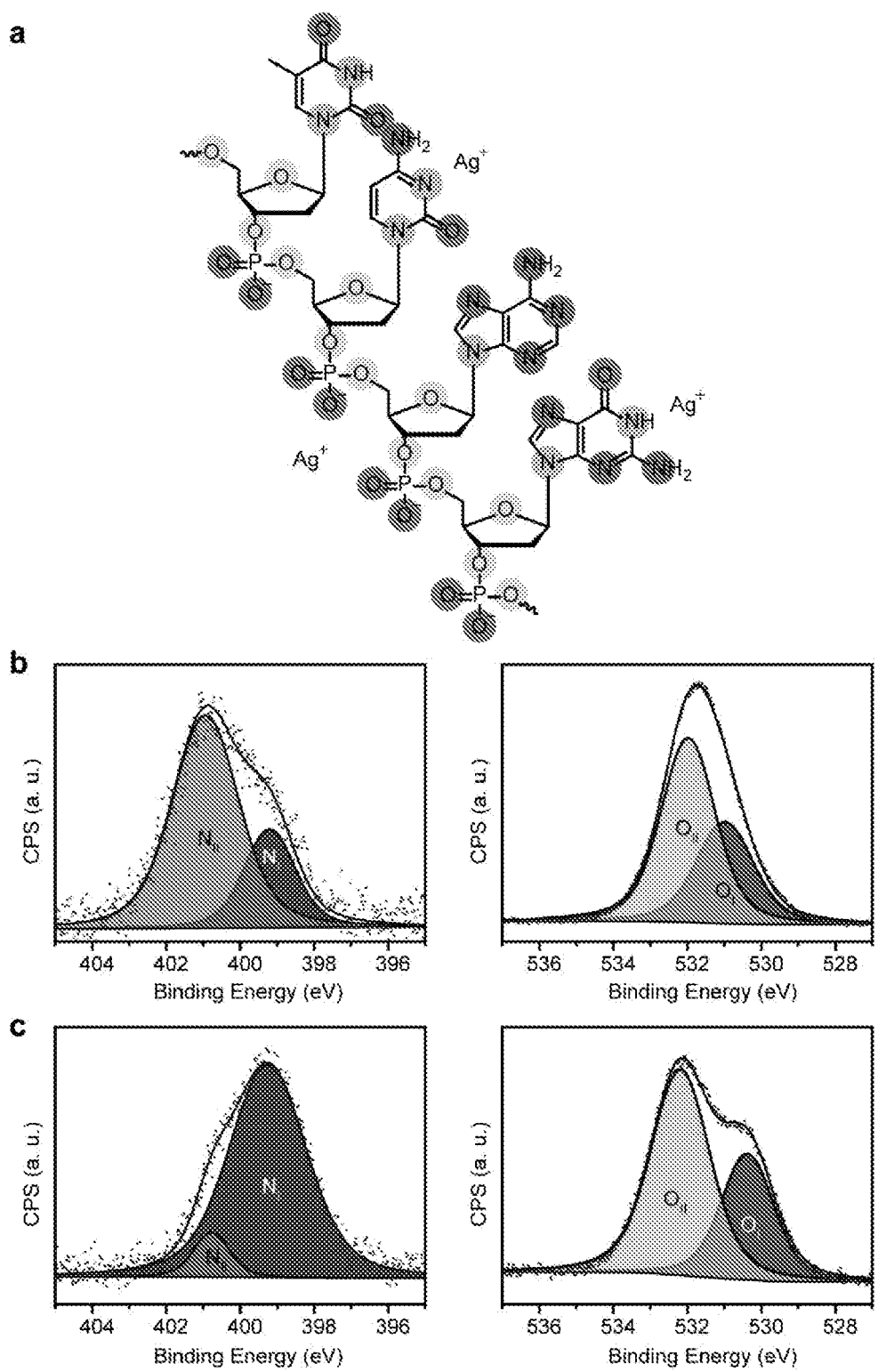
FIG. 11 shows (a) Schematic representation of a DNA strand (TCAG). (b) XPS spectra of RDs at N 1s core level peaks (left) and O 1s core level peaks (right) before $Ag^+$-stabilization. (c) Same data for Ag-RDs.

Further studies were carried out to determine how the addition of $Ag^+$ enhances the stability of DNA and PAE crystals. The materials analyses, including circular dichroism (CD; FIG. 10), X-ray photoelectron spectroscopy (XPS; FIG. 11), and inductively coupled plasma optical emission spectroscopy (ICP-OES; Table 4), complementarily substantiate that $Ag^+$ ions chemically bind to the DNA. For example, upon $Ag^+$ addition, conformational changes of the DNA can be observed by CD spectroscopy, as evidenced by the formation of negative bands around 275 nm.[3a, 3c, 3d] In addition, XPS shows a shift of the N 1s peak (N—C—O and N—C=O) to a lower binding energy (401 to 399 eV), a consequence of the increase in the electron density at the N atoms binding to $Ag^+$ ions.[9]

Figure 3:
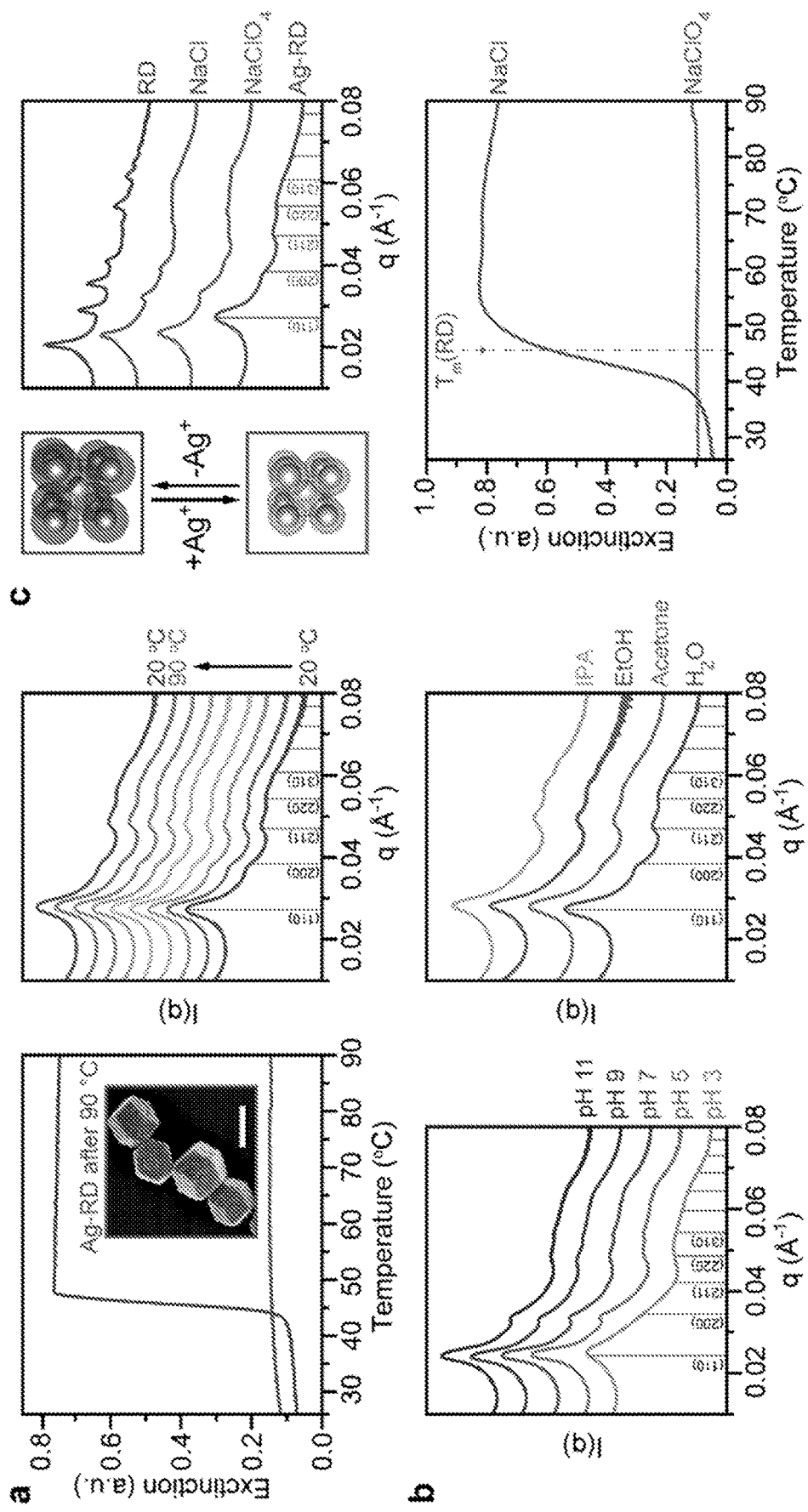
FIG. 3 shows (a) Melting curves (left) measured by variable-temperature UV-vis spectroscopy for RDs composed of 20 nm spherical Au nanoparticles suspended in 0.5 M NaCl (top trace), and Ag-RDs in water (bottom trace). An inset SEM image confirms that the Ag-RDs maintain the Wulff shape after heating at 90° C. SAXS patterns (right) for Ag-RDs in water do not change over the range of 20-90° C. Scale bar: 1 µm. (b) Ag-RDs can be transferred into variety of pH solutions (left), and solvents (acetone, ethanol, isopropyl alcohol) (right) while maintaining their symmetry and lattice parameters. (c) SAXS patterns (top) and variable-temperature UV-vis spectroscopy (bottom) show the reverse reaction from Ag-RD to RD by transferring to 0.5 M NaCl solution. By comparison with $NaClO_4$, $Cl^-$ is indeed responsible for the $Ag^+$ elimination.
Figure 12:
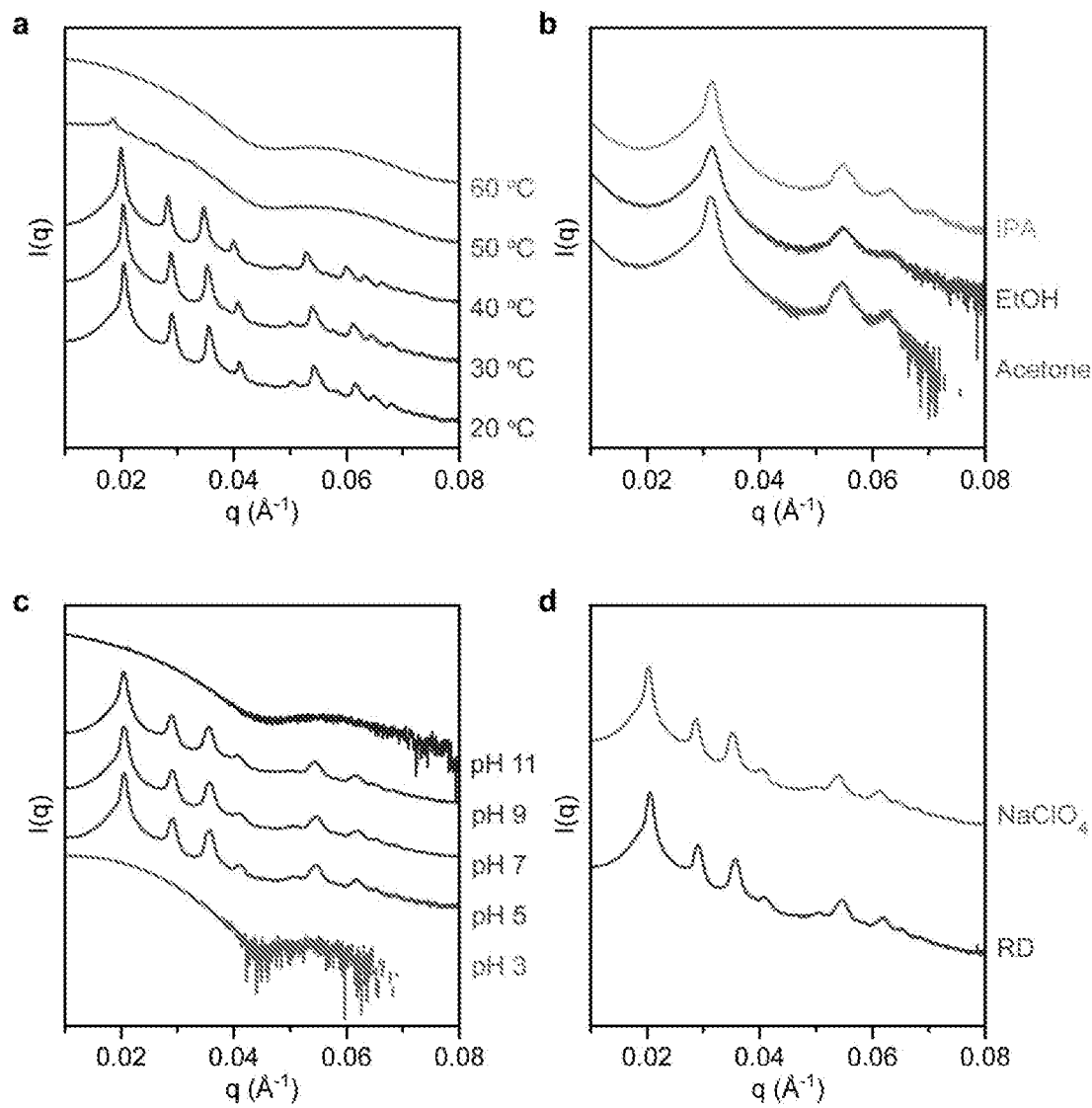
FIG. 12 depicts radially-averaged one-dimensional SAXS patterns of untreated RDs of 20 nm PAEs in (a) 0.5 M NaCl at 20-60° C., (b) acetone, ethanol, and isopropyl alcohol, (c) a variety of pH solutions, and (d) 0.5 M NaClO$_4$ solution.
Figure 13:
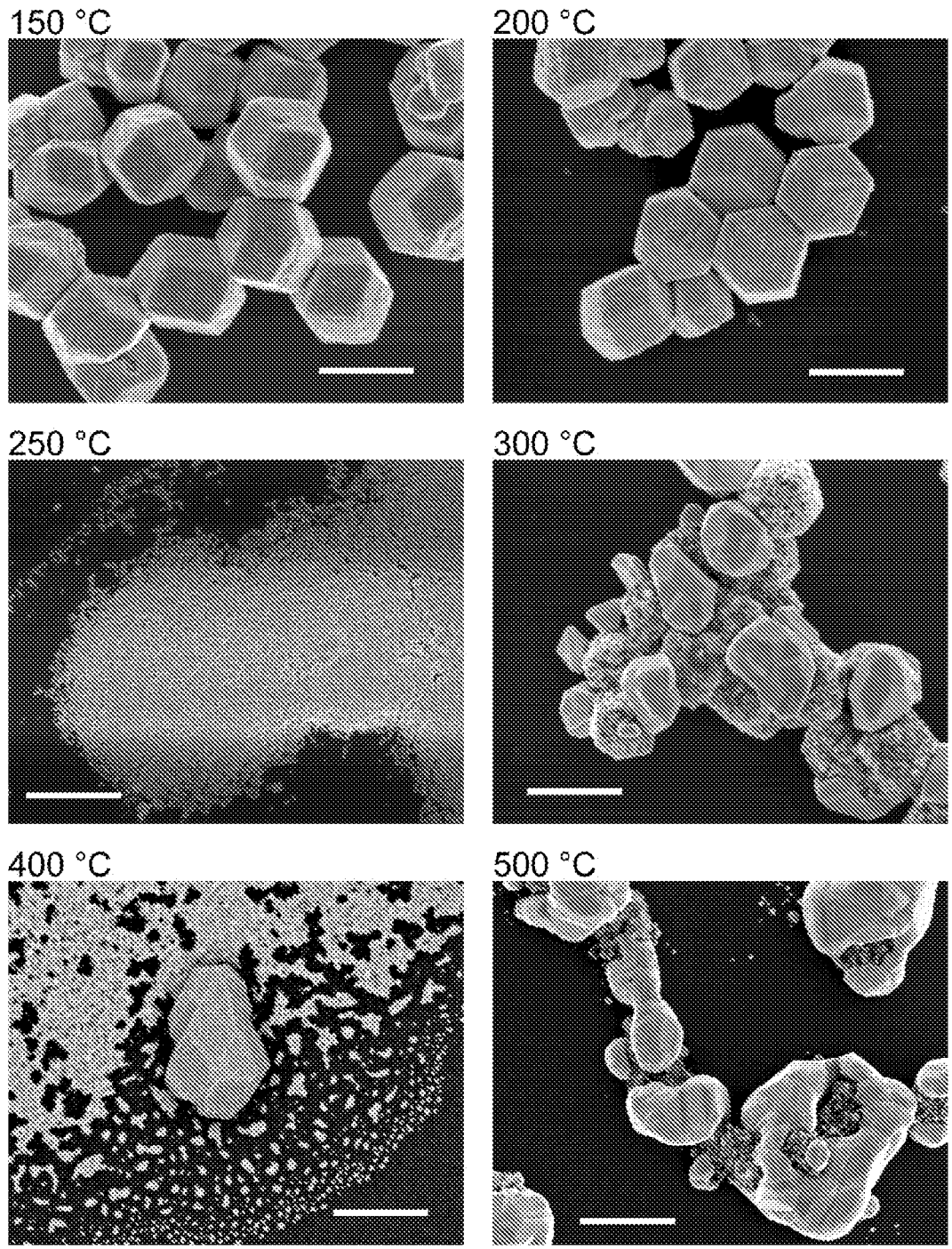
FIG. 13 shows SEM images of Ag-RDs after being heated in the solid state under air for 5 hours on Si wafers. The Ag-RDs remain intact up to 200° C. Above 250° C., the Ag-RDs start breaking and sintering. All scale bars: 1 μm.

Not only did $Ag^+$ stabilize PAE crystals in pure water, but it also prevented their thermal dissociation. As previously reported, $Ag^+$-coordinated base pairs are orders of magnitude stronger than canonical Watson-Crick base pairing.[3a] Indeed, this results in substantially increased DNA bond stability within the crystals. Variable-temperature UV-vis spectroscopy and SAXS confirmed this increased stability in water (FIG. 3a). Note that while the untreated RDs melt at 45.5° C. (FWHM≈2.5° C.) in aqueous 0.5 M NaCl, the Ag-RDs showed no evidence of melting from room temperature to 90° C. (FIG. 3a). Similarly, SAXS confirms that the Ag-RDs show no change in lattice structure in water at 90° C., whereas the bcc SAXS pattern for the untreated RDs disappears at and above 50° C. (FIG. 12). Note the RDs maintain their Wulff shape after heat treatment at 90° C. in water for 1 hour (FIG. 3a inset), and even in the solid state after being heated to 200° C. for 5 hours (FIG. 13).

Remarkably, the crystalline Ag-RDs were stable in aqueous media over the 5-11 pH range and in many organic solvents (acetone, ethanol, and isopropyl alcohol, FIG. 3b), as evidenced by SAXS. The effect of changes in pH were negligible above pH 5, but some peaks broadened at pH 3. At a pH below the pKa of the imino N3 group in cytosine (4.2),[10] $H^+$ effectively competes with $Ag^+$ for the binding sites (N atoms) in the nucleotide bases.[11] The robust nature and thermal stability of Ag-RDs in the solid state (FIG. 13) will be important as these structures become the basis for device components,[12] where they must be compatible with conventional lithographic procedures, including heat treatment and exposure to various types of photoresists (organic) and developers (typically basic solutions).[13]

The reversibility of the $Ag^+$-stabilization of PAE crystals was tested by a $Cl^-$-induced AgCl precipitation reaction. After two cycles of washing and resuspension in 0.5 M NaCl, SAXS peaks of the Ag-RDs shift to lower q, closer to the peak positions of the original RDs (FIG. 3c), which proves the expansion of the bcc crystal lattices. Importantly, the solution remains colorless indicating that the superlattices do not dissociate during $Ag^+$ ion extraction. However, the lattices post-extraction do melt with a melting temperature (Tm) of 44° C. (FWHM=8° C.), the value expected for $Ag^+$-free PAE crystals. The reversible contraction and expansion by the addition and extraction of $Ag^+$ can be repeated at least three times. To better understand this recovery process, a control sample was prepared with the Ag-RDs washed and re-dispersed in 0.5 M $NaClO_4$, which contains the same amount of $Na^+$ ions but anions that do not react with the $Ag^+$ in the superlattices. A similar but relatively modest shift of the SAXS peaks to lower q was observed, but interestingly, such crystals do not thermally decompose, even at 90° C. (FIG. 3c).

Figure 4:
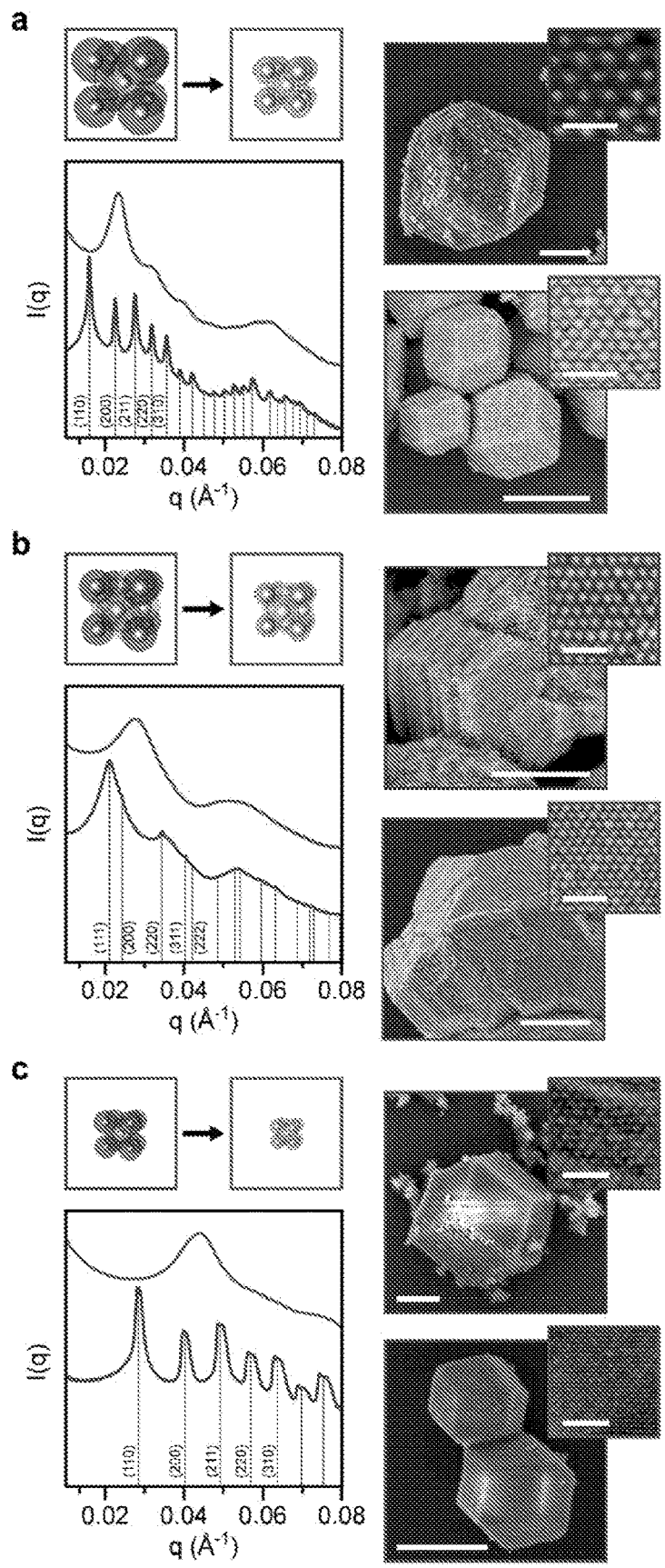
FIG. 4 depicts schematics for the unit cells, radially averaged one-dimensional SAXS patterns, and SEM images of untreated PAE crystals (bottom trace) and $Ag^+$-stabilized PAE crystals (top trace). (a) bcc superlattice of 20 nm nanoparticles with longer DNA linkers (Table 1), (b) fcc superlattice of 20 nm nanoparticles, and (c) bcc superlattice of 10 nm nanoparticles. Scale bars: 1 µm and 100 nm for insets.
Figure 5:
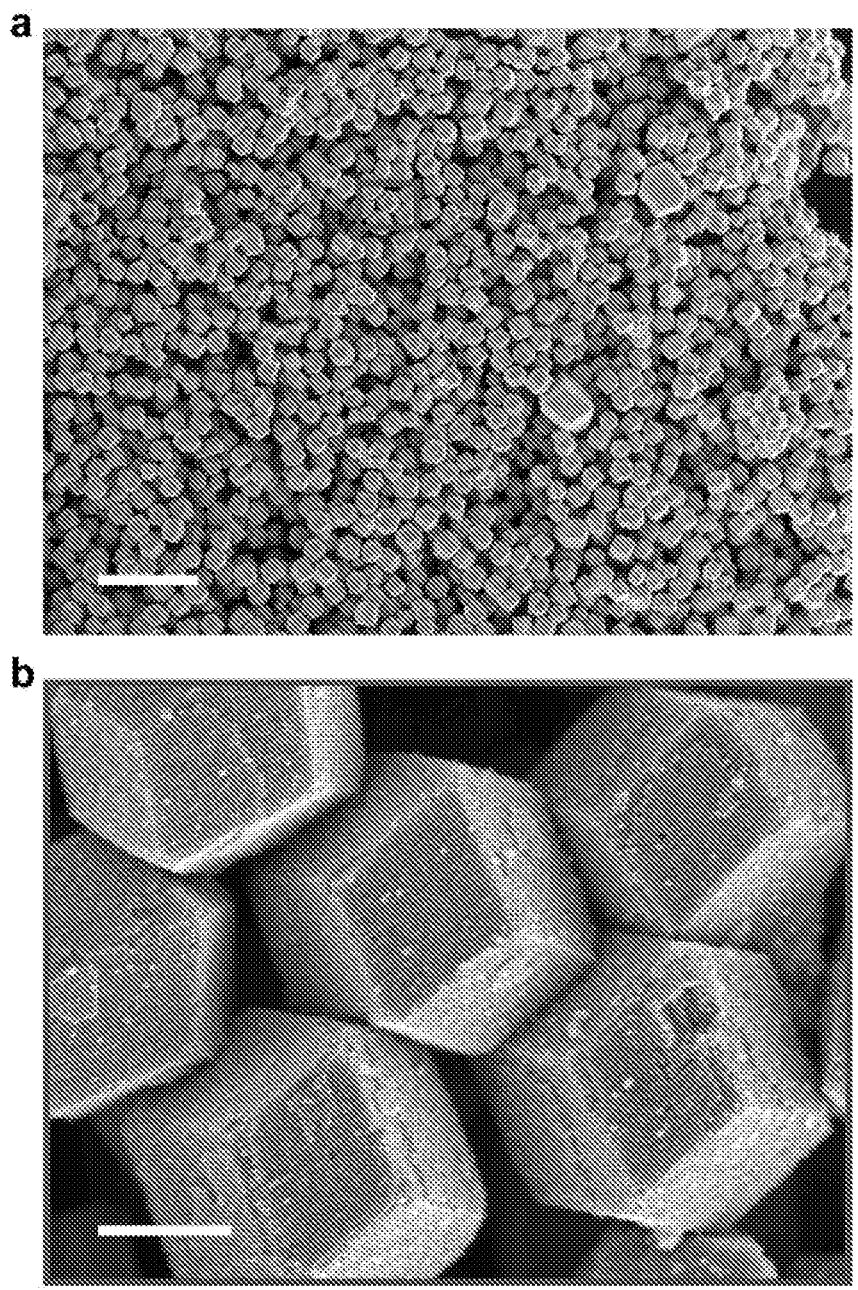
FIG. 5 shows (a) Large-scale synthesis (>mg) of rhombic dodecahedral PAE crystals in uniform and pure powder form. (b) A magnified image of the highlighted area in panel a. Scale bars: (a) 5 µm and (b) 500 nm.

To test the generality of the $Ag^+$-stabilizing process, colloidal crystals with different lattice parameters, symmetries, and core sizes were studied. Specifically, three different colloidal crystal systems were examined: (1) one with a bcc lattice symmetry but greater lattice spacing (Table 1), (2) one with a face-centered cubic (fcc) lattice symmetry, and (3) a bcc superlattice composed of smaller nanoparticles (10 nm diameter core). All three cases, consistent with the earlier results, showed the conservation of lattice symmetries with reduced lattice parameters, and could be stably transferred into water without salt, and eventually to the solid state for SEM (FIG. 4). Furthermore, by combining this method with density-based filtering,[7] is possible to obtain a large batch of uniform and pure stabilized colloidal crystals in powder form (FIG. 5).

Conclusion. As described and exemplified herein, the present disclosure provides a general method for stabilizing colloidal crystals made with nucleic acid (e.g., DNA) by integrating $Ag^+$ ions into their DNA bonds. Crystals treated in this manner can be studied and manipulated in media and at temperatures typically incompatible with such materials, and therefore, this technique will increase the scope of their utility, especially in the areas of optics, catalysis, electronics, and other applications where the pristine crystal habit and crystal symmetry are critical for device performance.[12, 14]

EXAMPLES

Example 1

Materials. Au nanoparticles were purchased from BBI via Ted Pella, Inc., and reagents for DNA synthesis were purchased from Glen Research. Chemicals, including NaCl, $AgNO_3$, $NaClO_4$, $NaH_2PO_4$, $Na_2HPO_4$, and sodium dodecyl sulfate (SDS) were purchased from Sigma-Aldrich. Milli-Q® water was used in all aqueous solutions.

Synthesis and characterization of DNA. All oligonucleotides used in this work synthesized on a MerMade 12 automated oligonucleotide synthesizer (BioAutomation) with reagents from Glen Research. Oligonucleotides were synthesized with 5' trityl group and purified with reverse-phase high-performance liquid chromatography (HPLC; Agilent), followed by standard deprotection procedures.[15] Matrix-assisted laser desorption ionization time-of-flight mass spectrometry (MALDI-TOF; AutoFlex-III, Bruker) was used to validate the synthesis and purification processes by checking the molecular weight of the oligonucleotides. The OligoAnalyzer tool (Integrated DNA Technologies) was used to predict the extinction coefficient and molecular weight of each DNA strand. The absorption at A=260 nm (Cary 5000 UV-vis spectrophotometer; Varian) was used to quantify the synthesized DNA strands.

The DNA design for the crystallization of programmable atom equivalents (PAEs) in this work follows the literature.[16] Briefly, Au nanoparticles were functionalized with one of two single-stranded 3'-propylthiol-modified "anchor" strands. To each of the "anchor" strands, a second "linker" strand was hybridized. Specific sequences used in this work are listed in Table 1.

TABLE 1

DNA sequences used herein.

| DNA Description | DNA Sequence (5' to 3') | SEQ ID NO: |
|---|---|---|
| A Anchor | TCA ACT ATT CCT ACC TAC (Spacer 18)$_2$-(CH$_2$)$_3$SH | 1 |
| A Linker | GTA GGT AGG AAT AGT TGA (Spacer 18) TTT CCT T | 2 |
| B Anchor | TCC ACT CAT ACT CAG CAA (Spacer 18)$_2$-(CH$_2$)$_3$SH | 3 |
| B Linker | TTG CTG AGT ATG AGT GGA (Spacer 18) AAG GAA A | 4 |
| Long A Linker | GTA GGT AGG AAT AGT TGA (Spacer 18) TTA CTG AGC AGC ACT GAT TT (Spacer 18) TTT CCT T | 5 |
| Long B Linker | TTG CTG AGT ATG AGT GGA (Spacer 18) TTA CTG AGC AGC ACT GAT TT (Spacer 18) AAG GAA A | 6 |
| Self-Complementary A Linker | GTA GGT AGG AAT AGT TGA (Spacer 18) GCG C | 7 |
| Duplexer for Block modular unit | AAA TCA GTG CTG CTC AGT AA | 8 |

"Spacer 18" refers to the six ethylene glycol units with modified phosphoramidites, which were manufactured by Glen Research.

Functionalization of nanoparticles with DNA. Au nanoparticles were functionalized with 3'-propylthiol-terminated oligonucleotides using literature procedures.[17] Briefly, thiolated oligonucleotides (Table 1 were treated with a 100 mM solution of dithiothreitol (DTT) in 0.17 M sodium phosphate buffer (pH=8) for 1 hour to deprotect the thiol terminals. Residuals from the deprotection reaction and excess DTT were removed with NAPTM-10 size exclusion columns (GE Healthcare). Thirty (30) mL of a commercial stock solution of citrate-capped 20 nm nanoparticles was incubated with these DNA (30 optical density (OD)) for 3 hours at room temperature. Phosphate buffer solution (PBS, pH=7.4) and SDS were added to the solution, and aqueous 2 M NaCl was added gradually over 3 hours until the final concentrations of phosphate buffer, SDS, and NaCl were 10 mM, 0.01%, and 0.5 M, respectively. After 12 hours, each nanoparticle solution was centrifuged (21,000 rcf) three times to remove excess DNA, with the supernatant removed each time. The particles were resuspended in 1 mL of 0.01 M PBS (pH=7.4), 0.5 M NaCl, and 0.01 wt % SDS. The concentration of each particle solution (A and B) was approximately 500 nM, quantified by UV-vis spectroscopy using known extinction coefficients for Au particles from the Ted Pella, Inc. website (http://www.tedpella.com/gold_html/gold-tec.htm).

Colloidal crystallization of PAEs. Rhombic dodecahedral PAE colloidal crystals (bcc lattice symmetry) were assembled by slowly cooling a solution of A- and B-type DNA-functionalized nanoparticles (5 nM each) with the respective DNA linker strands (3 µM each, Table 1 in 0.01 M PBS (pH=7.4), 0.5 M NaCl, and 0.01 wt % SDS. A thermocycler (ProFlex PCR System, Thermo Fisher Scientific) or a water bath equipped with an immersion circulator (AC200, Thermo Scientific) was used to slowly cool the reaction chamber containing the PAE solution, starting at 55° C. (about 10° C. above the melting temperature, and therefore, starting from dissociated free particles) to room temperature at a rate of 0.01° C. min$^{-1}$. A density-based filtering method was used to enhance the uniformity of the PAE crystals;[18] a 10% w/v dextran sulfate aqueous solution ($M_r$=500000 g mol$^{-1}$, $\rho$=1.058 g cm$^{-3}$) was placed beneath the same volume of the PAE solution before the slow-cooling process. During the slow-cooling, the density barrier keeps the free PAEs in the top layer from diffusing into the heavier dextran sulfate solution, and the sublayer captures only the sedimenting PAE crystals and quenches their growth.

Preparation of PAE crystals stabilized with Ag$^+$. When the solution reached room temperature, the slow-cooling process was complete, and the assembled PAE crystals were collected from the bottom of the reaction tube and the supernatant was removed and discarded. The crystals were washed three times with aqueous 0.5 M NaClO$_4$ containing 0.01 wt % SDS (this solution does not form precipitates with Ag$^+$ cations). To stabilize the microcrystals, 0.5 M AgNO$_3$ aqueous solution was rapidly added to the tube containing the PAE crystals, and the mixture was incubated for 12 hours at room temperature in the dark (alternatively for rapid stabilization, the mixture can be incubated for 5 minutes at 90° C.) to ensure Ag$^+$-stabilization. Finally, the Ag$^+$-stabilized crystals were washed three times with water, prior to characterization.

Silica encapsulation of PAE crystals. Prior to developing the method reported herein, a sol-gel process was used for embedding PAE crystals in silica.[19] Such structures can be imaged by SEM without significantly perturbing them. The matrix-embedded structures were prepared for comparison purposes with the Ag$^+$-stabilized architectures. Briefly, 400 µL aliquots of PAE crystal samples were diluted with 0.01 M sodium phosphate buffer (pH=7.4), 0.5 M NaCl, and 0.01 wt % SDS to a total 1 mL volume. Two (2) µL of N-trimethoxysilylpropyl-N, N, N-trimethylammonium chloride (50% in methanol, Gelest, Inc.) was added, and the vessel was placed on a shaker at 700 rpm for 20 min. Then, 4 µL of triethoxysilane (Sigma-Aldrich) was added, and the solution was placed on a shaker (700 rpm) for 12 hours at room temperature. The samples were washed three times and the silica-encased structures were collected each time by centrifugation (10 s, 10000 rpm), followed by removal of the supernatant and resuspension in 1 mL nanopure water.

Small-angle X-ray scattering studies. Synchrotron small-angle X-ray scattering (SAXS) experiments were conducted at the Dow-Northwestern-Dupont Collaborative Access Team (DND-CAT) beamline of the Advanced Photon Source (APS) at Argonne National Laboratory. All of the experiments were conducted with an X-ray wavelength of 1.24 Å (10 keV). The sample angle was calibrated with a silver behenate standard, and two sets of slits were used to define and collimate the beam. Samples were prepared in a 1.5 mm quartz capillary (Charles Supper Company, Inc.) and placed into the sample stage. Exposure times varied from 0.1 to 0.5 s, and scattered radiation was detected with a CCD area detector. 1D SAXS data presented with scattering intensity, I(q), as function of the scattering vector, q, was obtained by an azimuthal average of 2D scattering patterns.

$$q = \frac{4\pi \sin\theta}{\lambda}$$

where $\theta$ is half of the scattering angle and $\lambda$ is the wavelength of X-ray radiation. Scattering from the solution, capillary, and DNA were assumed to be negligible due to the orders of magnitude difference in the scattering associated with the Au nanoparticles. The space group assignment (Im$\bar{3}$m for bcc and Fm$\bar{3}$m for fcc) and interparticle spacing were determined by comparing the positions of experimental diffraction peaks to the predicted peaks. The structural parameters of these systems are provided in Table 3.

Variable-temperature UV-vis experiments. For melting experiments, 1 mL of each sample (total PAE concentration=1 nM) was loaded in a quartz cuvette with a small cavity at the bottom for a magnetic stir bar. UV-vis spectra were collected at 520 nm for the Au nanoparticles and 260 nm for the DNA on a Varian Cary 5000 UV-vis spectrometer, with the sample stage being heated from 25 to 65° C. (or to 90° C. for Ag$^+$-stabilized crystals) at 0.1° C. min$^{-1}$. The temperature was regulated with a Peltier heat pump attached to a six-cell holder, and the samples were tightly capped and continuously stirred throughout the experiment to facilitate thermal diffusion and to ensure the suspension of assemblies in the beam path.

Scanning electron microscopy. Scanning electron microscopy (SEM) images were acquired with a Hitachi SU8030 FE-SEM at the Northwestern University Atomic and Nanoscale Characterization Experimental Center (NU-ANCE). Approximate 5 µL samples were deposited on a O$_2$ plasma-cleaned Si wafer, and excess solvent was removed by pipette absorption. The images were acquired at a working distance of 4 mm with an electron beam energy of 5 kV and emission current of 15 µA. Energy-dispersive X-ray spectroscopy was carried out with an Oxford AZtec X-max 80 SDD EDS detector equipped on the SEM, at a working distance of 15 mm with an electron beam energy of 30 kV.

Inductively coupled plasma optical emission spectrometry. The P, Ag, and Au content in the DNA was quantitatively measured by inductively coupled plasma optical emission spectrometry (ICP-OES, iCAP 7600, Thermo Scientific) at the NU Quantitative Bio-element Imaging Center (QBIC). After the addition of AgNO$_3$ aqueous solution and incubation at 90° C. for 5 minutes, the samples were purified by NAPTM-5 size exclusion columns to remove the residual Ag+ ions and other smaller entities. Then, the Ag$^+$-incorporating DNA samples were digested by sonication in concentrated acid solution (HNO$_3$ and HCl) for 1 hour, followed by incubation at 55° C. for 12 hours. Before the measurement, the samples were diluted so the acid concentration was 3% HNO$_3$ and 2% HCl. Standards were prepared from analytical standard solutions purchased from Sigma-Aldrich.

It was found that no excess Ag$^+$ ions bind to the DNA duplexes; the Ag/base pair values do not exceed 0.45 even if a large excess of Ag$^+$ was used (Table 4). This result indicates that, on average, only one or less Ag$^+$ ion is attached to each base pair, but there still must be a nucleobase-dependence (for example, Ag$^+$ ions are not likely to bind to A bases). Considering approximately 60% of A-T contents in the DNA design, arithmetically, most of the C-G pairs may be transformed as metallo base-pairs, whereas the A-T pairs may remain in the Watson-Crick conformation, and minimal amount of Ag$^+$ may be bound to the backbone.

Figure 8:
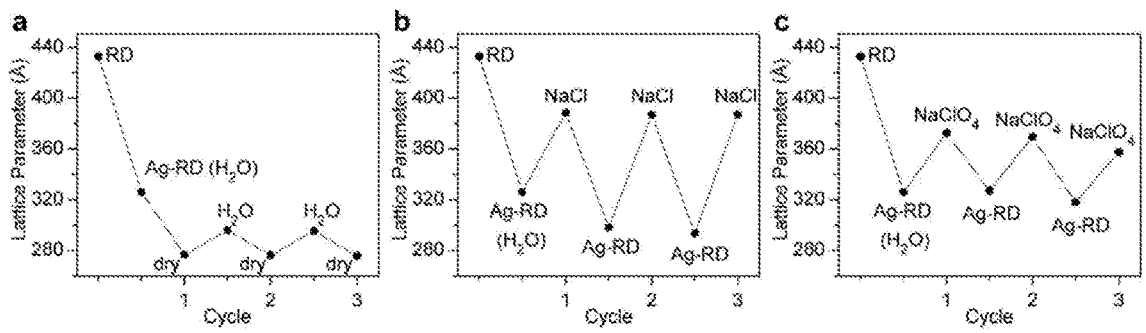
FIG. 8 shows the change in lattice parameters as a function of (a) dehydration, (b) addition of 0.5 M NaCl, and (c) addition of 0.5 M $NaClO_4$ over three cycles. The lattice parameters were calculated from SAXS measurements.

Circular dichroism studies. Circular dichroism (CD) spectra of the free DNA strands with or without Ag+-stabilization were recorded between λ=200-400 nm on Jasco J-1700 circular dichroism spectrometer at room temperature (FIG. 6). The samples were prepared as aqueous solutions with 10 μM of the DNA in 5 mM 3-(N-morpholino)propanesulfonic acid (MOPS) buffer (pH=7.0) and 2 mM NaCl (or NaClO$_4$ for samples containing silver), and either 0 or 4 equivalents of AgNO$_3$ to the number of base pairs was added to each sample. The measurements were performed after incubation at 90° C. for 5 minutes and cooling down to room temperature over 1 hour (FIG. 8).

Figure 9:
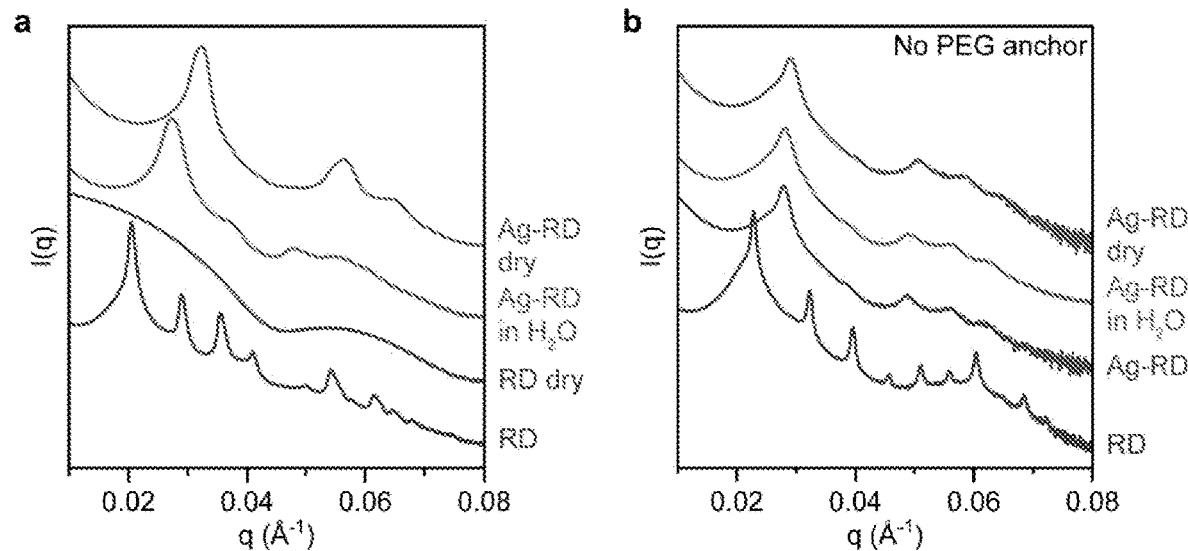
FIG. 9 shows (a) Radially-averaged one-dimensional SAXS patterns of RDs of 20 nm PAEs with two Spacer 18 units on the anchor DNA (A anchor and B anchor) in 0.5 M $NaClO_4$, the dried state of RDs, Ag-RDs of the same PAE system in water, and the dried state. (b) Comparison of SAXS patterns of RDs of 20 nm PAEs without Spacer 18 groups to Ag-RDs of 20 nm PAEs without Spacer 18 groups in 0.5 M AgNO3 solution, water, and dry state.

X-ray photoelectron spectroscopy. X-ray photoelectron spectroscopy (XPS, ESCALAB 250Xi, Thermo Scientific) was carried out on PAE crystals (FIG. 9). Ag$^+$-stabilized PAE crystals were prepared following the method described above, and a control sample without Ag$^+$ was washed with 0.5 M NH$_4$CH$_3$COO three times. Each sample was dropcast onto a highly oriented pyrolytic graphite (HOPG) substrates, and dried under vacuum for 24 hours, before the XPS measurements.

According to Volkov et al.,[20] the core level N 1s peaks of DNA can be decomposed into two peaks depending on their chemical states: N atoms near O (N3 atoms in T or C, and N1 atom in G, N$_{II}$ in the spectrum, FIG. 9 and the others (N$_I$). Similar to the literature, as a result of the Ag$^+$ addition to PAE crystals, an increase in the relative intensities of N$_I$ was observed, suggesting that Ag$^+$ binds to a fraction of the heterocyclic N$_{II}$ sites and the peak shifts to N$_I$. The changes in O peaks possibly indicate that Ag$^+$ ions are also adsorbed to the phosphate backbone, but it is difficult to deconvolute them from the background signals from adsorbents on the substrate and to derive a decisive conclusion.

Reversibility studies. Using AgCl precipitation, Ag$^+$ can be extracted from the Ag-RDs. In these experiments, the Ag-RDs were suspended in water and washed twice with aqueous 0.5 M NaCl containing 10 mM PBS and 0.01% SDS. SAXS and variable-temperature UV-vis spectroscopy (FIG. 2c) confirm the recovery of the as-synthesized structures with corresponding properties: post-extraction, the lattice parameter increased and the melting temperature returned to values observed for the as-synthesized Ag$^+$-free RDs. Additionally, the process is repeatable as observed by the re-stabilization of the superlattices where the NaCl-treated Ag-RDs were washed three times with aqueous 0.5 M NaClO$_4$ with 0.01% SDS and transferred to aqueous 0.5 M AgNO$_3$. The stabilization-destabilization processes can be carried out at least three times as confirmed by SAXS in FIG. 7b.

TABLE 2

List of sulfonic based pH buffers used in SAXS measurements.

| | | |
|---|---|---|
| pH 3 | Piperazine-N,N'-bis(3-propanesulfonic Acid) | PIPPS |
| pH 5 | 2-(N-Morpholino)ethanesulfonic acid | MES |
| pH 7 | 3-(N-Morpholino)propanesulfonic acid | MOPS |
| pH 9 | N-[Tris(hydroxymethyl)methyl]-3-aminopropanesulfonic acid | TAPS |
| pH 11 | 3-(Cyclohexylamino)-1-propanesulfonic acid | CAPS |

It is noteworthy that the choice of such sulfonic acid buffers was made to avoid any precipitation or reaction with Ag$^+$ in Ag-RDs. The concentration of the buffer solutions was 10 mM with 0.5 M NaClO$_4$.

TABLE 3

Experimental conditions and lattice parameters determined from SAXS.

| Particle size (nm) | DNA | Ag$^+$ | Solution | Space group | Lattice parameter (Å) |
|---|---|---|---|---|---|
| 20 | Normal A-B | no | NaClO$_4$ | $Im\bar{3}m$ | 432.97 |
| 20 | Normal A-B | no | acetone | $Im\bar{3}m$ | 284.58 |
| 20 | Normal A-B | no | IPA | $Im\bar{3}m$ | 282.56 |
| 20 | Normal A-B | no | ethanol | $Im\bar{3}m$ | 282.13 |
| 20 | Normal A-B | no | pH3 | N/A | N/A |
| 20 | Normal A-B | no | pH5 | $Im\bar{3}m$ | 431.46 |
| 20 | Normal A-B | no | pH7 | $Im\bar{3}m$ | 431.27 |
| 20 | Normal A-B | no | pH9 | $Im\bar{3}m$ | 433.86 |
| 20 | Normal A-B | no | pH11 | N/A | N/A |
| 20 | Normal A-B | no | NaClO$_4$ | $Im\bar{3}m$ | 435.32 |
| 20 | Normal A-B | no | dry | N/A | N/A |
| 20 | Longer A-B | no | NaClO$_4$ | $Im\bar{3}m$ | 557.95 |
| 20 | Self-complementary | no | NaClO$_4$ | $Fm\bar{3}m$ | 517.26 |
| 10 | Normal A-B | no | NaClO$_4$ | $Im\bar{3}m$ | 312.12 |
| 20 | Normal A-B | yes | AgNO$_3$ | $Im\bar{3}m$ | 326.20 |
| 20 | Normal A-B | yes | H$_2$O | $Im\bar{3}m$ | 327.23 |
| 20 | Normal A-B | yes | acetone | $Im\bar{3}m$ | 316.01 |
| 20 | Normal A-B | yes | IPA | $Im\bar{3}m$ | 314.05 |
| 20 | Normal A-B | yes | EtOH | $Im\bar{3}m$ | 314.68 |
| 20 | Normal A-B | yes | pH3 | $Im\bar{3}m$ | 353.56 |
| 20 | Normal A-B | yes | pH5 | $Im\bar{3}m$ | 361.28 |
| 20 | Normal A-B | yes | pH7 | $Im\bar{3}m$ | 362.73 |
| 20 | Normal A-B | yes | pH9 | $Im\bar{3}m$ | 369.31 |
| 20 | Normal A-B | yes | pH11 | $Im\bar{3}m$ | 364.90 |
| 20 | Normal A-B | yes | NaCl | $Im\bar{3}m$ | 388.44 |
| 20 | Normal A-B | yes | NaClO$_4$ | $Im\bar{3}m$ | 373.06 |
| 20 | Normal A-B | yes | dry | $Im\bar{3}m$ | 276.65 |
| 20 | Longer A-B | yes | H$_2$O | $Im\bar{3}m$ | 381.63 |
| 20 | Self-complementary | yes | H$_2$O | $Fm\bar{3}m$ | 390.29 |
| 10 | Normal A-B | yes | H$_2$O | $Im\bar{3}m$ | 201.6 |
| 20 | anchors without PEG | no | NaClO$_4$ | $Im\bar{3}m$ | 390.08 |
| 20 | anchors without PEG | yes | AgNO$_3$ | $Im\bar{3}m$ | 317.61 |
| 20 | anchors without PEG | yes | H$_2$O | $Im\bar{3}m$ | 316.06 |
| 20 | anchors without PEG | yes | dry | $Im\bar{3}m$ | 306.05 |

TABLE 4

Comparison of mass and molar contents of Ag per base pair from ICP-OES.

| Initial Ag (equiv. to base pair) | Measured Ag (equiv. to base pair) | Standard Deviation |
|---|---|---|
| 0 | 0.001 | 0.0007 |
| 0.25 | 0.251 | 0.0066 |
| 0.5 | 0.393 | 0.0020 |
| 2.5 | 0.435 | 0.0069 |
| 5 | 0.319 | 0.0082 |
| 10 | 0.290 | 0.0068 |
| 200 | 0.288 | 0.0543 |

Superlattice assembly. Rhombic dodecahedral PAE colloidal crystals (bcc lattice symmetry) were assembled by slowly cooling a solution of A- and B-type DNA-functionalized nanoparticles (5 nM each) with the respective DNA linker strands (3 μM each, Table 1), 0.01 M phosphate buffer (pH=7.4), 0.5 M NaCl, and 0.01 wt % SDS (see above for details). A density-based filtering method was used to enhance the uniformity of the PAE crystals;[7] a 10% w/v dextran sulfate aqueous solution ($M_r$=500000 g mol$^{-1}$, ρ=1.058 g cm$^{-3}$) was placed beneath the same volume of the PAE solution before the slow-cooling process. During the slow-cooling, the density barrier keeps the free PAEs in the top layer from diffusing into the heavier dextran sulfate solution, and the sublayer captures only the sedimenting PAE crystals and quenches their growth.

Preparation of PAE crystals stabilized with Ag$^+$. The assembled superlattices were washed three times with aqueous 0.5 M NaClO$_4$ containing 0.01 wt SDS (this solution does not form precipitates with Ag$^+$ cations). To stabilize the microcrystals, 0.5 M aqueous AgNO$_3$ was rapidly added to the tube containing the superlattices, and the mixture was incubated for 12 hours at room temperature to ensure complete reaction. Alternatively, qualitatively similar results could be obtained by heating at 90° C. for 5 minutes, instead of waiting for 12 hours. Finally, the Ag$^+$-stabilized superlattices were washed three times with water, prior to exposing them to different conditions.

REFERENCES

[1] a) C. A. Mirkin, R. L. Letsinger, R. C. Mucic, J. J. Storhoff, *Nature* 1996, 382, 607; b) S. Y. Park, A. K. Lytton-Jean, B. Lee, S. Weigand, G. C. Schatz, C. A. Mirkin, *Nature* 2008, 451, 553; c) R. J. Macfarlane, B. Lee, M. R. Jones, N. Harris, G. C. Schatz, C. A. Mirkin, *Science* 2011, 334, 204; d) E. Auyeung, T. I. Li, A. J. Senesi, A. L. Schmucker, B. C. Pals, M. O. de la Cruz, C. A. Mirkin, *Nature* 2014, 505, 73; e) M. N. O'Brien, H. X. Lin, M. Girard, M. O. de la Cruz, C. A. Mirkin, *J. Am. Chem. Soc.* 2016, 138, 14562; f) P. Cigler, A. K. R. Lytton-Jean, D. G. Anderson, M. G. Finn, S. Y. Park, *Nat. Mater.* 2010, 9, 918; g) Y. Zhang, F. Lu, K. G. Yager, D. van der Lelie, O. Gang, *Nat. Nanotech.* 2013, 8, 865; h) Y. F. Wang, Y. Wang, X. L. Zheng, E. Ducrot, M. G. Lee, G. R. Yi, M. Weck, D. J. Pine, *J. Am. Chem. Soc.* 2015, 137, 10760; i) Y. F. Wang, I. C. Jenkins, J. T. McGinley, T. Sinno, J. C. Crocker, *Nat. Commun.* 2017, 8, 14173.

[2] E. Auyeung, R. J. Macfarlane, C. H. Choi, J. I. Cutler, C. A. Mirkin, *Adv. Mater.* 2012, 24, 5181.

[3] a) S. M. Swasey, L. E. Leal, O. Lopez-Acevedo, J. Pavlovich, E. G. Gwinn, *Sci. Rep.* 2015, 5, 10163; b) X. Chen, A. Karpenko, O. Lopez-Acevedo, *ACS Omega* 2017, 2, 7343; c) H. H. Liu, F. S. Shen, P. Haruehanroengra, Q. Q. Yao, Y. S. Cheng, Y. Q. Chen, C. Yang, J. Zhang, B. X. Wu, Q. Luo, R. X. Cui, J. X. Li, J. B. Ma, J. Sheng, J. H. Gan, *Angew. Chem. Int. Ed.* 2017, 56, 9430; d) S. M. Swasey, E. G. Gwinn, *New J. Phys.* 2016, 18, 045008.

[4] a) E. Ennifar, P. Walter, P. Dumas, *Nucleic Acids Res.* 2003, 31, 2671; b) Y. Miyake, H. Togashi, M. Tashiro, H. Yamaguchi, S. Oda, M. Kudo, Y. Tanaka, Y. Kondo, R. Sawa, T. Fujimoto, T. Machinami, A. Ono, *J. Am. Chem. Soc.* 2006, 128, 2172.

[5] a) A. Ono, S. Cao, H. Togashi, M. Tashiro, T. Fujimoto, T. Machinami, S. Oda, Y. Miyake, I. Okamoto, Y. Tanaka, *Chem. Commun.* 2008, 39, 4825; b) H. Urata, E. Yamaguchi, Y. Nakamura, S. Wada, *Chem. Commun.* 2011, 47, 941; c) T. Funai, Y. Miyazaki, M. Aotani, E. Yamaguchi, O. Nakagawa, S. Wada, H. Torigoe, A. Ono, H. Urata, *Angew. Chem. Int. Ed.* 2012, 51, 6464; d) J. Kondo, Y. Tada, T. Dairaku, Y. Hattori, H. Saneyoshi, A. Ono, Y. Tanaka, *Nat. Chem.* 2017, 9, 956.

[6] M. R. Jones, N. C. Seeman, C. A. Mirkin, *Science* 2015, 347, 1260901.

[7] T. Oh, J. C. Ku, J. H. Lee, M. C. Hersam, C. A. Mirkin, *Nano Lett.* 2018, 18, 6022.

[8] a) J. A. Mason, C. R. Laramy, C. T. Lai, M. N. O'Brien, Q. Y. Lin, V. P. Dravid, G. C. Schatz, C. A. Mirkin, *J. Am. Chem. Soc.* 2016, 138, 8722; b) G. K. Williamson, W. H. Hall, *Acta. Metall. Mater.* 1953, 1, 22.

[9] I. L. Volkov, A. Smirnova, A. A. Makarova, Z. V. Reveguk, R. R. Ramazanov, D. Y. Usachov, V. K. Adamchuk, A. I. Kononov, *J. Phys. Chem. B* 2017, 121, 2400.

[10] R. M. Izatt, J. J. Christensen, J. H. Rytting, *Chem. Rev.* 1971, 71, 439.

[11] I. Okamoto, K. Iwamoto, Y. Watanabe, Y. Miyake, A. Ono, *Angew. Chem. Int. Ed.* 2009, 48, 1648.

[12] a) D. J. Park, C. Zhang, J. C. Ku, Y. Zhou, G. C. Schatz, C. A. Mirkin, *Proc. Natl. Acad. Sci. U.S.A* 2015, 112, 977; b) M. B. Ross, C. A. Mirkin, G. C. Schatz, *J. Phys. Chem. C* 2016, 120, 816.

[13] M. J. Madou, Fundamentals of microfabrication: the science of miniaturization, CRC Press, Boca Raton, Fla. 2002.

[14] a) L. Sun, H. X. Lin, K. L. Kohlstedt, G. C. Schatz, C. A. Mirkin, *Proc. Natl. Acad. Sci. U.S.A* 2018, 115, 7242; b) E. Auyeung, W. Morris, J. E. Mondloch, J. T. Hupp, O. K. Farha, C. A. Mirkin, *J. Am. Chem. Soc.* 2015, 137, 1658; c) J.-H. Choi, H. Wang, S. J. Oh, T. Paik, P. S. Jo, J. Sung, X. Ye, T. Zhao, B. T. Diroll, C. B. Murray, C. R. Kagan, *Science* 2016, 352, 205.

[15] E. Auyeung, J. I. Cutler, R. J. Macfarlane, M. R. Jones, J. S. Wu, G. Liu, K. Zhang, K. D. Osberg, C. A. Mirkin, *Nat. Nanotech.* 2012, 7, 24.

[16] S. Y. Park, A. K. Lytton-Jean, B. Lee, S. Weigand, G. C. Schatz, C. A. Mirkin, Nature 2008, 451, 553.

[17] S. J. Hurst, A. K. R. Lytton-Jean, C. A. Mirkin, Anal. Chem. 2006, 78, 8313.

[18] T. Oh, J. C. Ku, J. H. Lee, M. C. Hersam, C. A. Mirkin, Nano Lett. 2018, DOI: 10.1021/acs.nanolett.8b02910.

[19] E. Auyeung, R. J. Macfarlane, C. H. Choi, J. I. Cutler, C. A. Mirkin, Adv. Mater. 2012, 24, 5181.

[20] I. L. Volkov, A. Smirnova, A. A. Makarova, Z. V. Reveguk, R. R. Ramazanov, D. Y. Usachov, V. K. Adamchuk, A. I. Kononov, J. Phys. Chem. B 2017, 121, 2400.

What is claimed:

1. A method comprising
admixing a colloidal crystal with a silver ion source to form a stabilized colloidal crystal,
wherein
the colloidal crystal comprises nanoparticles modified on the nanoparticle surface with nucleic acids ("anchor strands") and arranged in a lattice pattern; and
the stabilized colloidal crystal exhibits a lattice parameter (Å) of at least 15% smaller than that of the colloidal crystal, and exhibits improved stability in one or more of the following: water, an organic solvent, a pH of 5 to 11, a temperature of 25° C. to 200° C.; or in a solid state compared to the colloidal crystal.

2. The method of claim 1, wherein nanoparticles comprise gold nanoparticles.

3. The method of claim 1, wherein the anchor strands comprise DNA.

4. The method of claim 1, wherein the anchor strands further comprise a polyethylene glycol spacer.

5. The method of claim 1, wherein the lattice pattern is cubic, body-centered cubic, face-centered cubic, trigonal, tetragonal, body-centered tetragonal, orthorhombic, body-centered orthorhombic, face-centered orthorhombic, base-centered orthorhombic, hexagonal, monoclinic, or base-centered monoclinic.

6. The method of claim 1, wherein the silver ion source comprises silver nitrate.

7. The method of claim 1, wherein the admixing is at room temperature for 12 to 36 hours.

8. The method of claim 1, wherein the admixing is at 85° C. to 100° C. for 1 to 90 minutes.

9. The method of claim 1, further comprising washing the stabilized colloidal crystals with water.

10. The method of claim 1, further comprising preparing the colloidal crystal by
admixing a solution of a first nanoparticle and a second nanoparticle, optionally in the presence of a linker strand, under conditions to form the colloidal crystal via hybridization of the first nanoparticle and the second nanoparticle, and optionally the linker strand, wherein the first nanoparticle anchor strand, the second nanoparticle anchor strand, and optionally the linker strand comprise complementary sequences to hybridize.

11. The method of claim 10, further comprising cooling the solution from a temperature of (i) 50° C. to 75° C. down to (ii) room temperature.

12. The method of claim 11, wherein the cooling is at a rate of 0.01° C./min to 0.1° C./min.

13. The method of claim 10, wherein the linker strand comprises a nucleic acid sequence sufficiently complementary at a first portion to hybridize with the first nanoparticle anchor strand and sufficiently complementary at a second portion to hybridize with the second nanoparticle anchor strand.

14. The method of claim 10, wherein the solution of first nanoparticle and second nanoparticle and optional linker strand is above a dextran sulfate aqueous solution such that the colloidal crystals precipitate into the dextran sulfate aqueous solution.

15. The method of claim 10, further comprising isolating the colloidal crystals from the solution of first nanoparticle and second nanoparticle and optional linker strand.

16. The method of claim 15, wherein the isolating is via filtration.

17. The method of claim 1, further comprising drying the stabilized colloidal crystals.

18. The stabilized colloidal crystal prepared by the method of claim 1.

* * * * *